United States Patent
Nakamura et al.

(10) Patent No.: US 8,698,081 B2
(45) Date of Patent: Apr. 15, 2014

(54) PATTERN INSPECTION APPARATUS AND PATTERN INSPECTION METHOD

(75) Inventors: Takayuki Nakamura, Tokyo (JP); Tsutomu Murakawa, Tokyo (JP)

(73) Assignee: Advantest Corp., Tokyo (JP)

( * ) Notice: Subject to any disclaimer, the term of this patent is extended or adjusted under 35 U.S.C. 154(b) by 0 days.

(21) Appl. No.: 13/317,860

(22) Filed: Oct. 31, 2011

(65) Prior Publication Data
US 2013/0068947 A1 Mar. 21, 2013

Related U.S. Application Data

(63) Continuation of application No. PCT/JP2010/056814, filed on Apr. 16, 2010.

(30) Foreign Application Priority Data

Jun. 19, 2009 (JP) .................................. 2009-146990

(51) Int. Cl.
*H01J 37/28* (2006.01)
(52) U.S. Cl.
CPC ....................................... *H01J 37/28* (2013.01)
USPC .......................................................... 250/310
(58) Field of Classification Search
CPC ............................................... H01J 2237/2817
USPC .......................................................... 250/310
See application file for complete search history.

(56) References Cited

U.S. PATENT DOCUMENTS

| | | | |
|---|---|---|---|
| 6,252,412 B1 | 6/2001 | Talbot et al. | |
| 2002/0117635 A1 | 8/2002 | Shinada et al. | |
| 2003/0029998 A1* | 2/2003 | Matsumoto et al. | 250/307 |
| 2003/0063792 A1* | 4/2003 | Hiroi et al. | 382/149 |
| 2003/0089851 A1 | 5/2003 | Katagami et al. | |
| 2003/0201391 A1 | 10/2003 | Shinada et al. | |
| 2003/0206027 A1 | 11/2003 | Nozue et al. | |
| 2005/0043903 A1* | 2/2005 | Nara et al. | 702/35 |
| 2005/0205781 A1* | 9/2005 | Kimba | 250/311 |
| 2005/0238221 A1* | 10/2005 | Hirano et al. | 382/144 |
| 2006/0038986 A1* | 2/2006 | Honda et al. | 356/237.1 |
| 2006/0243908 A1* | 11/2006 | Shinada et al. | 250/310 |
| 2007/0230770 A1* | 10/2007 | Kulkarni et al. | 382/149 |
| 2009/0041335 A1* | 2/2009 | Matsui et al. | 382/149 |

(Continued)

FOREIGN PATENT DOCUMENTS

| | | |
|---|---|---|
| DE | 10 2004 030 122 | 1/2006 |
| JP | 2000-294183 | 10/2000 |

(Continued)

*Primary Examiner* — Jack Berman
*Assistant Examiner* — James Choi
(74) *Attorney, Agent, or Firm* — Muramatsu & Associates

(57) ABSTRACT

The pattern inspection apparatus includes: an irradiator irradiating a sample with an electron beam; an electron detector detecting an amount of electrons generated on the sample having a pattern formed thereon, by the irradiation of the electron beam; an image processor generating a SEM image of the pattern on the basis of the electron amount; and a controller acquiring defect position information on the pattern formed on the sample from an optical defect inspection device. The controller specifies a defect candidate pattern from the SEM image on the basis of the defect position information and judges whether a defect in the defect candidate pattern is to be transferred onto a wafer. The controller determines a view field of the SEM image on the basis of the defect position information and specifies the defect candidate pattern from image information on patterns displayed in the view field.

13 Claims, 9 Drawing Sheets

(56) References Cited

U.S. PATENT DOCUMENTS

| | | | |
|---|---|---|---|
| 2010/0196804 A1* | 8/2010 | Murakawa et al. | 430/5 |
| 2011/0133066 A1* | 6/2011 | Nozoe et al. | 250/252.1 |
| 2013/0070078 A1* | 3/2013 | Takagi et al. | 348/80 |

FOREIGN PATENT DOCUMENTS

| | | |
|---|---|---|
| JP | 2005-301156 | 10/2005 |
| JP | 2005-309140 | 11/2005 |
| JP | 2009-025221 | 2/2009 |

* cited by examiner

N1: 1234.56nm²
N2: 1234.67nm²
N3: 1234.78nm²
N4: 1234.89nm²
N5: 1235.12nm²
N6: 1234.98nm²
N7: 1234.87nm²
N8: 1234.76nm²
N9: 1234.65nm²

N1: 1234.56nm²
N9: 1234.65nm²
N2: 1234.67nm²
N8: 1234.76nm²
N3: 1234.78nm²
N7: 1234.87nm²
N4: 1234.89nm²
N6: 1234.98nm²
N5: 1235.12nm²

↑ area smallness

↓ area largeness

PATTERN INSPECTION APPARATUS AND PATTERN INSPECTION METHOD

CROSS-REFERENCE TO RELATED APPLICATIONS

This application is a continuation of prior International Patent Application No. PCT/JP2010/056814, filed on Apr. 16, 2010, which claims priority of provisional Japanese Patent Application No. 2009-146990, filed on Jun. 19, 2009, and the entire contents of which are incorporated herein by reference.

BACKGROUND OF THE INVENTION

1. Field of the Invention

The embodiment discussed herein are related to a pattern inspection apparatus and a pattern inspection method, and particularly, to a pattern inspection apparatus and a pattern inspection method which are capable of extracting pattern defects difficult to be identified visually in a SEM image.

2. Description of the Related Art

In a lithographic step in a semiconductor manufacturing process, a pattern formed on a photomask is transferred by exposure onto a wafer by using an exposure apparatus. If there is a defect or a strain in the pattern formed on this photomask, exposure accuracy is deteriorated, for example, the pattern is not transferred to a desired position, or the pattern shape becomes inaccurate. In order to prevent such deterioration in exposure accuracy, inspection is carried out on a photomask to find positional errors and defects.

As a method of inspecting a photomask, there is an inspection method utilizing a SEM image of a mask which is taken by a scanning electron microscope. The scanning electron microscope irradiates and scans a region within an electron scanning range with the incident electrons, acquires secondary electrons emitted from a sample by way of a scintillator, acquires SEM image data by converting an amount of the acquired electrons into luminance, and displays a SEM image on a display device.

For example, inspection using a line width of a pattern formed on a mask is carried out in accordance with the following procedures. A predetermined range of a pattern formed on a photomask is displayed on a display unit. Then, an electron beam aimed at a measurement point within the displayed range, and the measurement point is irradiated with the electron beam. Next, a waveform of luminance distribution is acquired based on secondary electrons reflected from the measurement point. Thereafter, pattern edge positions are determined by analyzing the waveform of luminance distribution, and a line width is defined. A judgment is made as to whether or not this line width is within an acceptable error range, thereby determining quality of the photomask.

Meanwhile, defects on the pattern are visually inspected by displaying a pattern image on a monitor. In this visual inspection, it is difficult to carry out the accurate inspection because the determination of the pattern quality varies depending on the inspector.

With respect to this problem, Japanese Laid-open Patent Publication No. 2000-294183 describes the following technique for inspecting shapes of fine patterns. In the technique, reference image data corresponding to variations in the concentration difference and the shape difference is generated based on a plurality of pieces of image data of fine quality product. Then, inter-image calculation is performed on the reference image data and inspection target image data to extract difference image data. Thereafter, the difference image data is compared with a predetermined threshold to extract portions with concentration defect and portions with shape defect.

Further, there is also proposed a defect inspection system which detects pattern defects by using an optical defect inspection device, observes images of the detected defect by using an observation device such as a SEM, and analyzes the defects.

An optical defect inspection device in the defect inspection system described above is able to specify patterns including defects and store positions of the defects as coordinate data. Such a defect inspection system is required to promptly determine the positions of the defects detected by the inspection device within a substrate by using the observation device.

For example, to share a coordinate system between the optical defect inspection device and the observation device such as the SEM, an image of a predetermined pattern on a substrate is detected and the coordinate system is corrected based on a position of this pattern.

However, even if coordinates of a position of a defect pattern are detected by the optical defect inspection device, the following problem may occur. Consider a case where the inspection device and the observation device respectively use different pattern detection methods and have different detection accuracies, for example, a case where the inspection device is of an optical type but the observation device is of an electron beam type as described above. In such a case, the same pattern may not be detected by both the inspection device and the observation device. As a consequence, there may arise a problem in which, even if a coordinate position detected by the optical defect inspection device is used, in the SEM, the coordinate position indicates a position of a pattern without any defects.

Meanwhile, sizes to be defined as defects are becoming smaller in recent years and it is extremely difficult to visually judge such defects in SEM images. In this respect, currently, presence and absence of the defects are judged by using a simulation image to be transferred onto a wafer such as by a wafer plane inspection (WPI) method, and enormous costs are incurred for operations to analyze the defects.

Note that, a defect pattern can be specified even if the coordinates are displaced from each other, provided that the pattern is isolated, for example. However, it is difficult to specify a defect pattern if there are a plurality of similar patterns located adjacent to one another.

SUMMARY OF THE INVENTION

The present invention has been made in view of the above-described problems of the related art and an object thereof is to provide a pattern inspection apparatus and a pattern inspection method capable of automatically detecting a pattern with a defect which is hard to be identified visually in a SEM image.

The problems described above can be solved by a pattern inspection apparatus including: an irradiator configured to irradiate a sample with an electron beam; an electron detector configured to detect an amount of electrons generated on the sample by the irradiation of the electron beam, the sample having a pattern formed thereon; an image processor configured to generate a SEM image of the pattern on the basis of the amount of the electrons; and a controller configured to acquire defect position information on the pattern formed on the sample from an optical defect inspection device. The controller specifies a defect candidate pattern from the SEM image on the basis of the defect position information and judges whether or not a defect in the defect candidate pattern is to be transferred onto a wafer.

In the pattern inspection apparatus according to the aspect described above, the controller may determine a view field of the SEM image on the basis of the defect position information and specify the defect candidate pattern from image information on patterns displayed in the SEM image in the view field. The controller may specify a reference pattern serving as a reference from patterns displayed in the SEM image, compare the reference pattern with other similar patterns, and specify, as the defect candidate pattern, at least any of a pattern largely different in area from the reference pattern and a pattern having a low degree of coincidence in pattern shape with the reference pattern. The controller may set an average value of areas of a plurality of similar patterns in the view field as a threshold and specify a pattern having an area least different from the threshold as the reference pattern. The controller may perform a correlation analysis between the reference pattern and other patterns in the view field and specify, as the defect candidate pattern, any one of a pattern having the lowest hit rate and a pattern most different from the reference pattern in area. The controller may compare a position of each of the defect candidate patterns with a defect position detected in the optical defect inspection device and specify the defect candidate pattern located at a position closest to the defect position as the defect candidate pattern.

Moreover, in the pattern inspection apparatus according to the aspect described above, the controller may extract a difference between the reference pattern and the defect candidate pattern, compare the difference with a transfer judgment reference defined in advance, and judge whether or not the defect in the defect candidate pattern is to be transferred onto the wafer. The transfer judgment reference may be defined based on at least any of an area difference of the extracted difference, a distance difference in an X direction or a Y direction, and an inscribed circle inside the extracted difference.

According to another aspect of the present invention, a pattern inspection method is provided which is to be executed by the pattern inspection apparatus according to the above-described aspect. The pattern inspection method is applicable to a pattern inspection apparatus including an irradiator configured to irradiate a sample with an electron beam, an electron detector configured to detect an amount of electrons generated on the sample by irradiation of the electron beam, the sample having a pattern formed thereon, and an image processor configured to generate image data of the pattern on the basis of the amount of the electrons. The method includes the steps of: acquiring defect position information on a pattern having a defect from an optical defect inspection device; determining a view field of a SEM image on the basis of the defect position information and acquiring the SEM image; specifying a reference pattern serving as a reference from patterns displayed in the SEM image; comparing the reference pattern with other patterns and thus specifying a defect candidate pattern including a defect; and judging whether or not the defect of the specified defect candidate pattern is a defect to be transferred onto a wafer.

In the pattern inspection method according to the aspect, in the step of specifying the reference pattern, an average value of areas of a plurality of similar patterns in the view field may be set as a threshold and a pattern least different from the threshold may be set as the reference pattern.

In the pattern inspection method according to the aspect, in the step of specifying the defect candidate pattern including a defect, a pattern most different from the reference pattern in area among other patterns in the view field is set as the defect candidate pattern. In the step of specifying the defect candidate pattern, a correlation analysis may be performed between the reference pattern and other patterns in the view field and a pattern having the lowest degree of coincidence with the reference pattern may be set as the defect candidate pattern. The step of specifying the defect candidate pattern may include the steps of: extracting a first defect candidate pattern having the defect by use of a difference between an area of the reference pattern and each of areas of the other patterns; extracting a second defect candidate pattern having the defect by a correlation analysis between the reference pattern and the other patterns in the view field, and setting, as the defect candidate pattern, a defect candidate pattern having a shorter distance to a defect position acquired from the optical defect inspection device, among the first defect candidate pattern and the second defect candidate pattern.

In the present invention, in order to observe a pattern including a defect detected by the optical defect inspection device in a SEM image, a position of the defect of the pattern is acquired from the optical defect inspection device. This position does not completely match a coordinate position in the SEM. Therefore, the pattern including the defect is specified in the SEM in the following manner. Namely, the areas of the respective similar patterns which are present in the view field of the SEM and an average area of the similar patterns are calculated. Then, the pattern whose area is closest to the average area is determined as the reference pattern. Next, correlations between the reference pattern and other patterns are obtained, and the pattern having the lowest correlation is set as the pattern including the defect. Then, the judgment is made as to whether or not the defect is the defect to be transferred onto the wafer.

In this way, it is possible to automatically detect a pattern including a defect which is not visually detectable.

DESCRIPTION OF THE EMBODIMENT

An embodiment of the present invention will be described below with reference to the accompanying drawings.

First, a configuration of a scanning electron microscope to be used as a pattern inspection apparatus will be described. Second, a process to detect a pattern including a defect in a SEM image will be described.

(Configuration of Scanning Electron Microscope)

Figure 1:
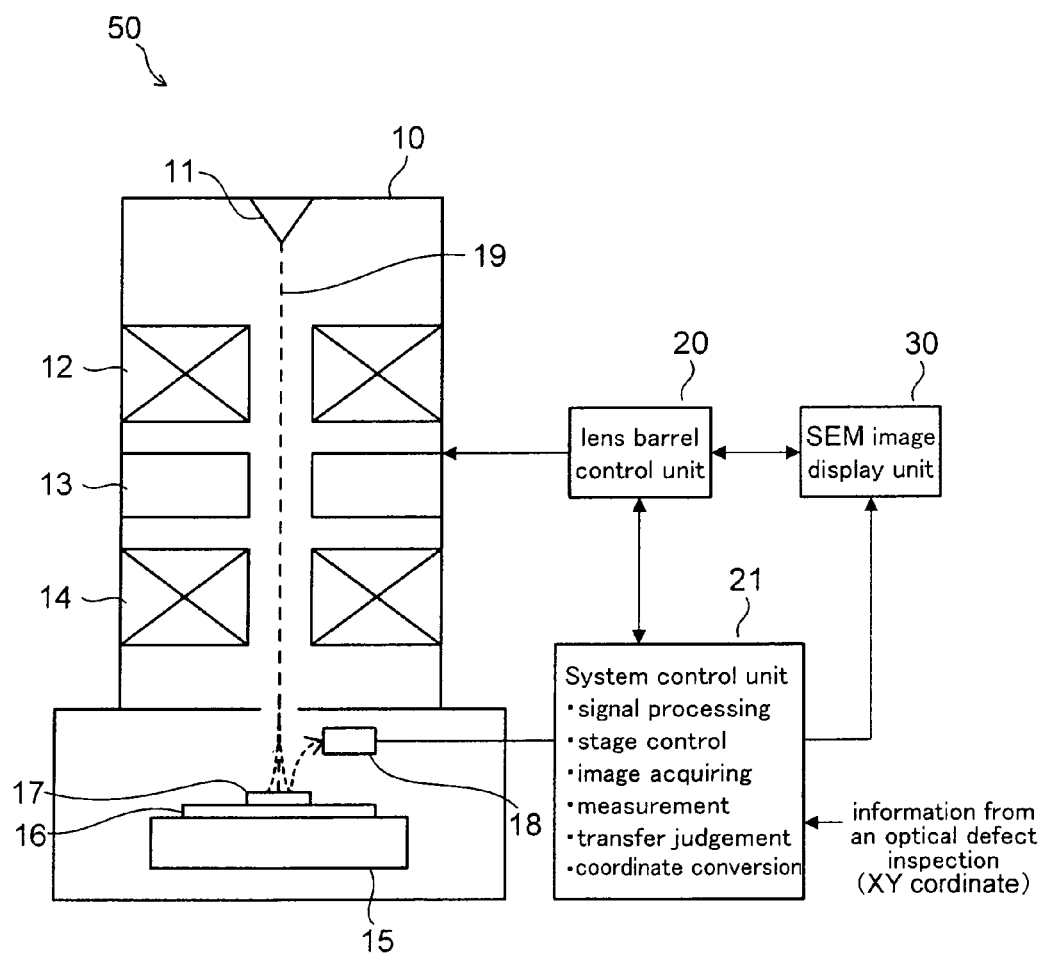
FIG. 1 is a configuration diagram of a scanning electron microscope used in an embodiment of the present invention.

FIG. 1 is a configuration diagram of a scanning electron microscope used in an embodiment of the present invention.

This scanning electron microscope 50 can be roughly divided into an electron scanning unit 10, a lens barrel control unit 20, a SEM image display unit 30, and a system control unit 21 configured to control the respective units of the electron scanning unit 10, the lens barrel control unit 20, and the SEM image display unit 30.

The electron scanning unit 10 includes an electron gun 11, a condensing lens 12, a deflecting coil 13, an objective lens 14, a movable stage 15, and a sample holder 16.

Charged particles 19 emitted from the electron gun 11 are caused to pass through the condenser lens 12, the deflecting coil 13, and the objective lens 14 and to irradiate a sample 17 on the movable stage 15.

The sample 17 is two-dimensionally scanned with the charged particles 19 (a primary electron beam) being irradiated thereon, and secondary electrons emitted from an irradiated region are detected by an electron detector 18 formed of a scintillator or the like. An amount of the detected secondary electrons is converted into a digital amount by an AD converter in the system control unit 21 and is stored in a memory as image data. The image data is converted into luminance signals and is displayed on the SEM image display unit 30. The image data are arranged in a two-dimensional array in the same arrangement as the corresponding scanning positions of the primary electron beam on the sample 17, and thus a two-dimensional digital image is obtained. Each pixel in this two-dimensional digital image expresses luminance data in information amount of 8-bits.

An electron deflection amount of the deflecting coil 13 and an image scanning amount of the SEM image display unit 30 are controlled by the lens barrel control unit 20.

Meanwhile, in addition to the signal process and the image acquisition process described above, the system control unit 21 performs stage control in which the stage is moved to obtain a SEM image with a designated view field.

Moreover, as described later in detail, the system control unit 21 acquires information (XY coordinates) on a position of a pattern including a defect from an optical defect inspection device and performs coordinate conversion. Further, the system control unit 21 performs edge detection of patterns displayed in the SEM image and calculation of areas of the patterns by using programs for performing these processes, then specifies a pattern having a defect out of the patterns displayed in the SEM image, and then performs a process of judging whether or not the defect is a defect to be transferred onto a wafer.

(Automatic Detection of Defect Pattern in SEM Image)

Next, automatic detection of a defect pattern in a SEM image will be described.

In this embodiment, automatic detection of a defect pattern is carried out in two-step processes, namely, (1) a process of specifying a defect pattern in a SEM image by using coordinate information and the like of the defect pattern from the optical defect inspection device, and (2) a process of judging whether or not the specified defect of the pattern is a defect to be transferred onto a wafer.

Figure 2:
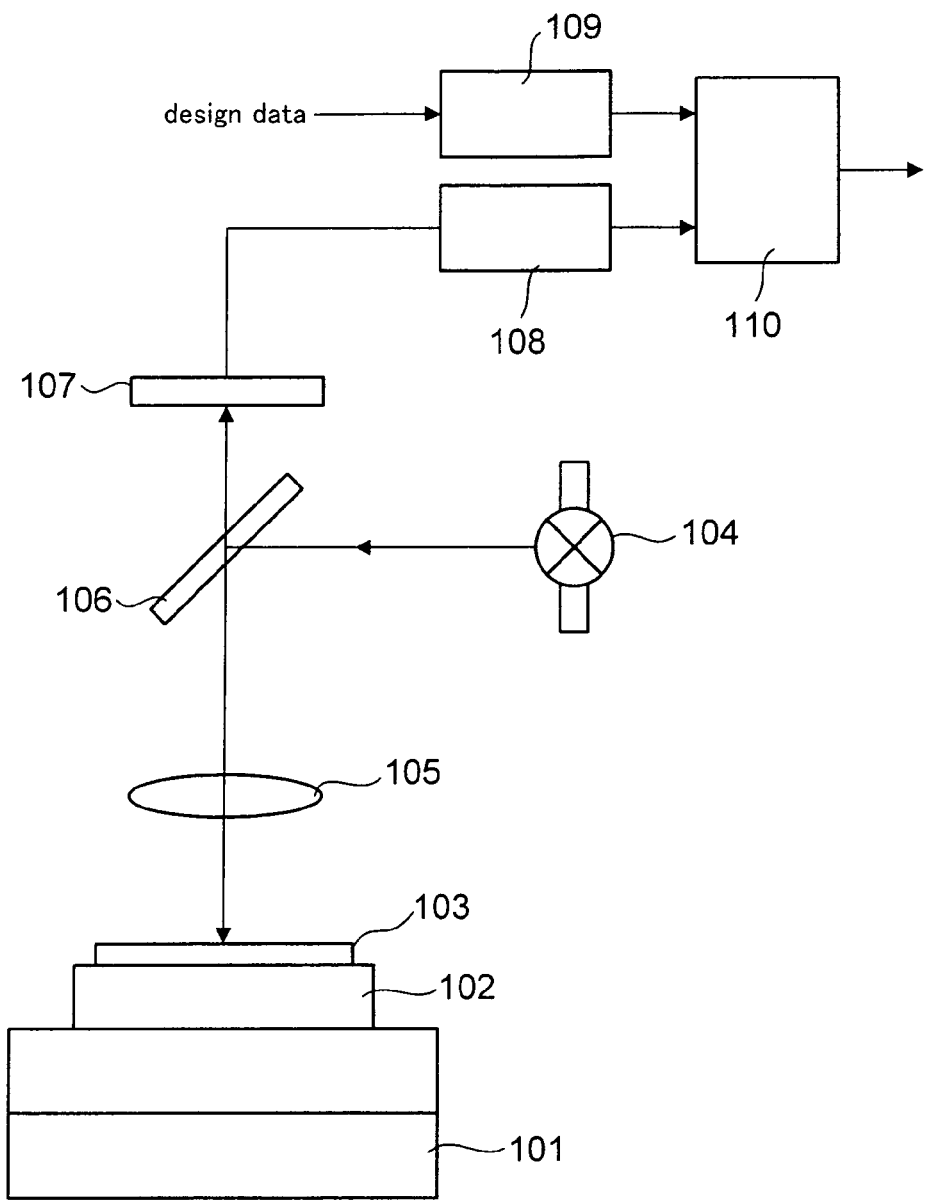
FIG. 2 is a configuration diagram showing an example of an optical defect inspection device.

FIG. 2 is a diagram showing an example of the optical defect inspection device. As shown in FIG. 2, a wafer 103 being an inspection target is placed on a stage 102 disposed on an XY stage 101. A half mirror 106 configured to direct illumination light from an illumination light source 104 toward the wafer 103 is provided above the wafer 103, and the light reflected by the half mirror 106 passes through an objective lens 105 and illuminates the wafer 103. Reflected light from the wafer 103 passes through the objective lens 105 and the half mirror 106 and is received as detected light by a detector 107 such as a CCD image sensor. Then, the detected light received by the detector 107 is converted into digital image data by an A/D converter 108 and signal comparing means 110 compares the digital image data with design data generated by a design data pattern generation circuit 109. If there is a portion where the signals of the digital image data and the design data do not match in this comparison process, then presence of a defect is determined.

The pattern inspection apparatus acquires information (XY coordinates) on a position of the defect in the pattern detected by this optical defect inspection device, determines a view field based on the XY coordinate position, and acquires a SEM image. Among the patterns displayed as the acquired SEM image, the same pattern as the defect pattern detected by the optical defect inspection device is detected and set as a defect candidate pattern. Further, the process of judging whether or not the detected defect candidate pattern is the pattern to be transferred onto the wafer is executed to specify the defect pattern.

Here, this embodiment is intended for a case where a plurality of patterns supposedly having the same shape are repeatedly formed.

Figure 3A:
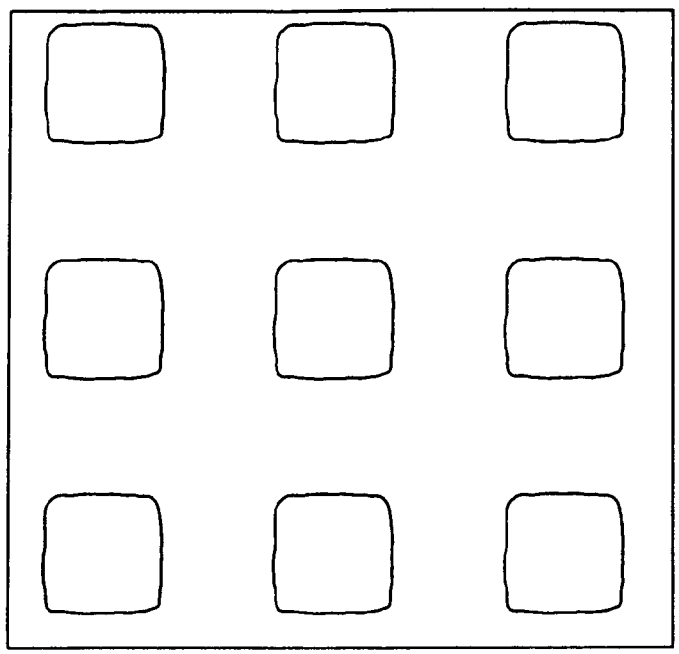
FIGS. 3A and 3B are views each showing an example of a pattern including a defect.
Figure 3B:
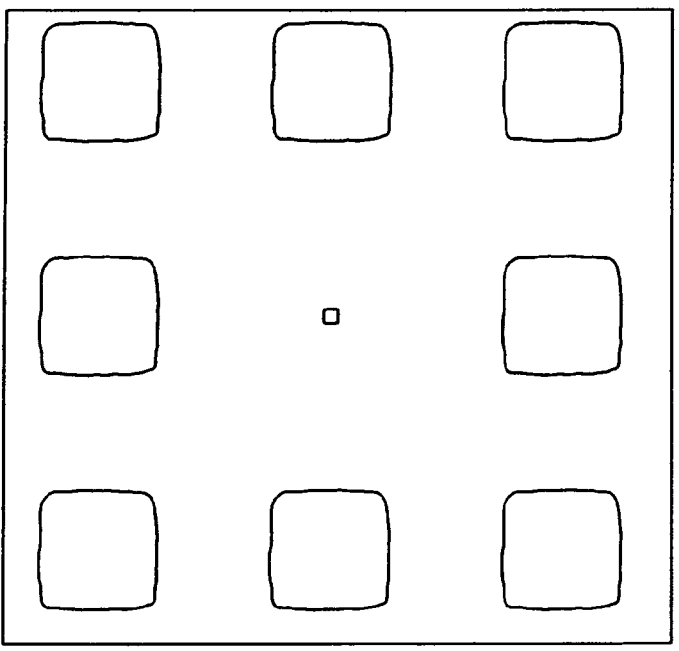

FIGS. 3A and 3B show examples of the displayed SEM images. In each of FIGS. 3A and 3B, nine similar patterns which are supposed to have shapes identical to one another are displayed in a view field. Each of these SEM images is an image in which position coordinates of a defect acquired from the optical defect inspection device is located at a central position.

FIG. 3A is an example in which the patterns supposed to have shapes identical to one another are displayed, the patterns including a defect pattern. As shown in the drawing, when patterns having identical shapes are repeatedly displayed, it is difficult to find a defect visually out of a displayed SEM image.

In this case, the coordinate systems are not entirely the same between the optical defect inspection device and the SEM. Therefore, even if the coordinate position of the defect pattern is located at the central position of the SEM image, it is not possible to directly determine that the pattern displayed at the central position is the one having the defect.

On the other hand, in FIG. 3B, a pattern obviously different from the neighboring patterns is displayed near the center of the SEM image. If there is such a pattern, it is possible to find a defect visually.

In this embodiment, the defect pattern is automatically detected from the information on the SEM image in which the identical patterns are repeatedly displayed as shown in FIG. 3A. A method of such automatic detection will be described below with reference to a flowchart in FIG. 4 and from FIGS. 5A to 9B.

Figure 4:
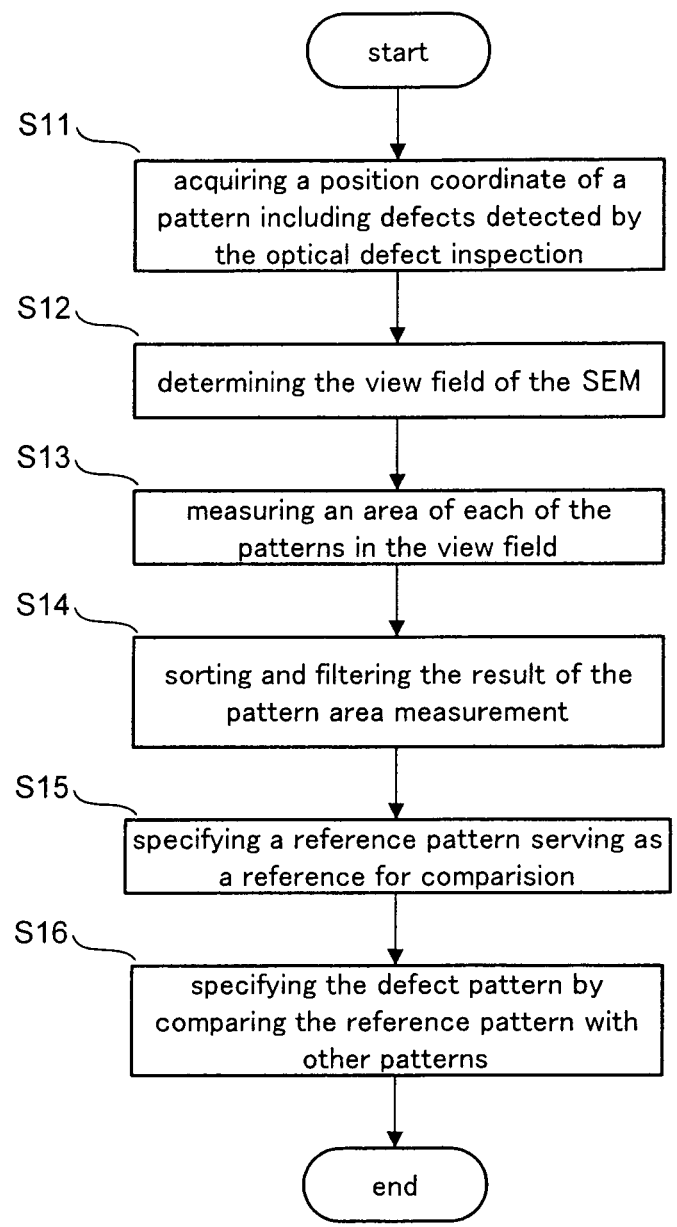
FIG. 4 is a flowchart showing an example of a process of extracting the pattern including the defect.

FIG. 4 is a flowchart showing an example of the process of specifying the defect candidate pattern out of the processes of detecting the defect pattern in the SEM image.

Figure 5A:
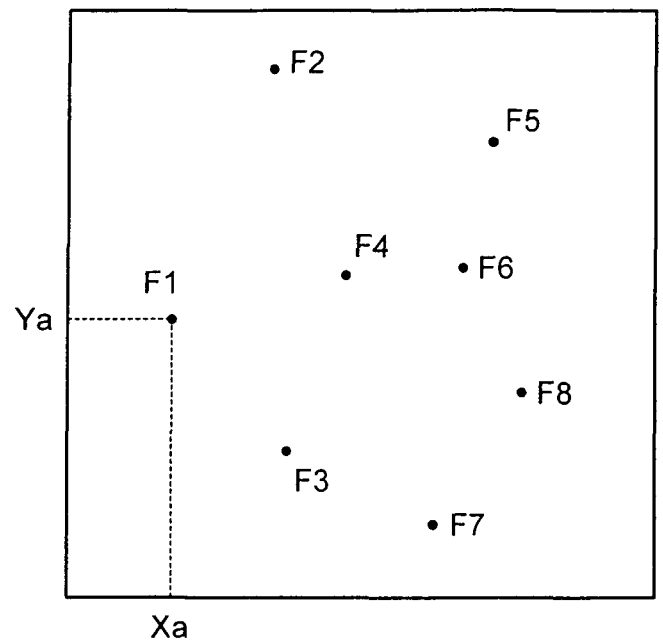
FIGS. 5A and 5B are views showing an example of positional coordinates of the defects.

First, the position coordinates of a pattern including defects detected by the optical defect inspection device are acquired in step S11. FIG. 5A shows positions of defects detected in a view field range of the optical defect inspection device. For example, defects of the pattern are detected in eight positions of F1 to F8. A defect position F1 is a position of (Xa, Ya) in XY coordinates, in which the point of origin is a lower left corner in the view field range in FIG. 5A.

Figure 5B:
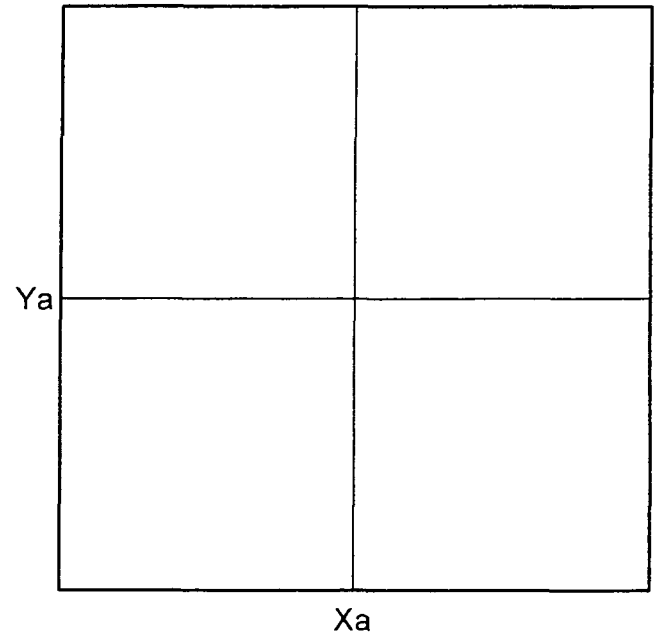

Next, the view field of the SEM is determined in step S12. The view field of the SEM image is determined based on the coordinate positions of the defects in the optical defect inspection device acquired in step S11. For example, as shown in FIG. 5B, the coordinate position (Xa, Ya) of the position F1 is located at the center of the view field. Here, the display of the patterns is omitted in FIG. 5B. However, in the actual implementation, the SEM image including the plurality of patterns will be displayed.

Figures 6A, 6B, 6C:
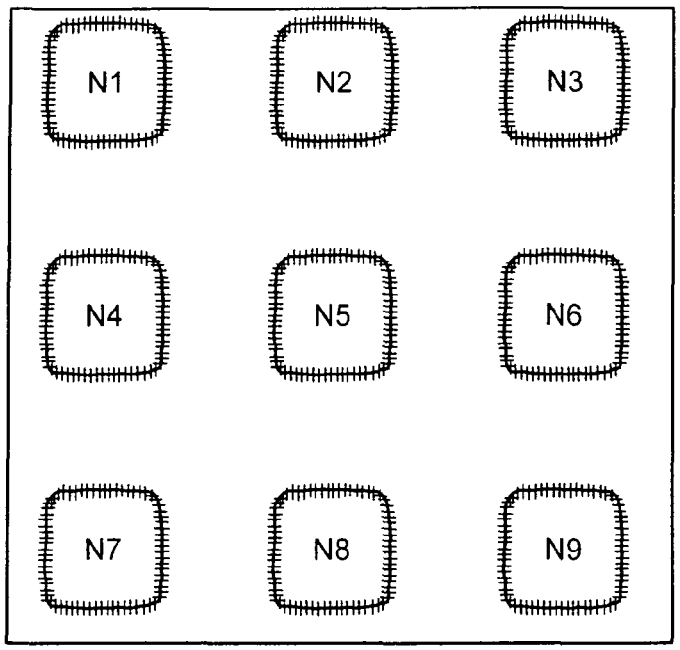
FIGS. 6A to 6C are views for explaining the process of extracting the pattern including the defect (area measurement of the patterns).

Next, an area of each of the patterns in the view field is measured in step S13. Prior to the area measurement, the respective patterns displayed in the SEM image are numbered. FIG. 6A shows an example in which nine patterns displayed in the SEM image are numbered from N1 to N9.

In order to perform the area measurement of each of the patterns accurately, a contour of each of the patterns is measured with high accuracy and the area is calculated based on the contour data. As shown in the patterns N1 to N9 in FIG. 6A, the contour of each of the patterns is measured by calculating edge positions from a line profile provided along lines perpendicular to the periphery of the corresponding pattern, and from the like.

Figure 7:
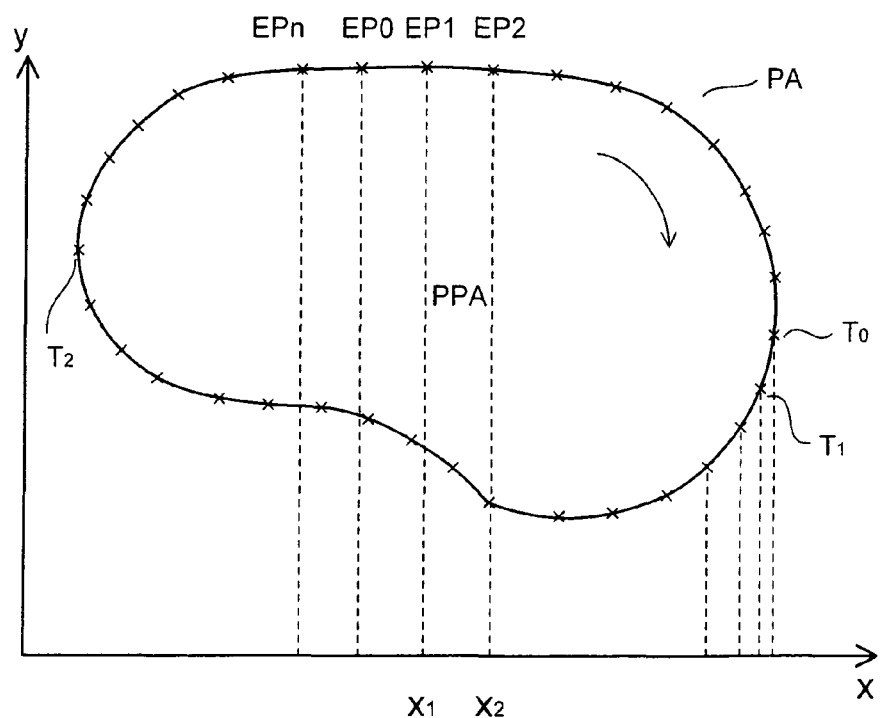
FIG. 7 is a view for explaining the area measurement of the patterns.

For example, it is assumed that n+1 pieces of edge positions are detected in the periphery of the pattern as shown in FIG. 7, and that a k-th edge position is defined as $EP_k (x_k, y_k)$.

The area S of the pattern is calculated from the following formula by using all the detected edge positions and applying a trapezoidal rule.

$$S = \sum_{k=1}^{n} \left( (X_k - X_{k-1}) \times \frac{(Y_k + Y_{k-1})}{2} \right) + (X_0 - X_n) \times \frac{(Y_0 + Y_n)}{2}$$

In the example of FIG. 7, calculation of an area of each of trapezoidal regions defined by the corresponding ones of the edge positions from $T_2$ to $T_0$ on an upper side of a pattern PA allows, for example an area of a region $(x_1 x_2 EP_1 EP_2)$ to be calculated, the region $(x_1 x_2 EP_1 EP_2)$ being a region combing a region PPA formed by dividing the pattern PA and a region not including the pattern. In the meantime, calculation of an area of each of trapezoidal regions defined by the corresponding ones of the edge positions from $T_1$ to $T_2$ on a lower side of the pattern PA allows an area of the region not including the pattern to be calculated.

Accordingly, the area of the pattern PA can be calculated by adding the areas of the trapezoidal regions defined by the edge positions from $T_2$ to $T_0$ on the upper side of the pattern PA to each other and then subtracting the areas of the trapezoidal regions defined by the edge positions from $T_1$ to $T_2$ on the lower side of the pattern PA.

In other words, the area of the pattern is calculated by adding the areas of the trapezoidal shapes in which the values of X coordinates of the edge positions are in a range of $X_k - X_{k-1} > 0$ to each other and subtracting the areas of the trapezoidal shapes in which the values of x coordinates are in a range of $X_k - X_{k-1} < 0$.

In step S14 of FIG. 4, results of the pattern area measurement of the calculated in step S13 are sorted and filtered. FIGS. 6B and 6C show an example of a process performed on the results of the pattern area measurement.

FIG. 6B shows the results of the area measurement performed for the respective patterns N1 to N9 of FIG. 6A. Meanwhile, FIG. 6B shows a case where the areas of the respective patterns N1 to N9 are sorted.

Note that, in the example of FIG. 6A, the entire pattern is displayed for each of the nine patterns in the SEM image. However, there may also be a case in which only a portion of a pattern is displayed depending on the view field. In that case, such a pattern is excluded from the inspection target. For example, information on the pattern area is acquired in advance from design data, and filtering is executed to exclude patterns having the areas equal to or below 50% of the acquired pattern area from the inspection target.

Next, a reference pattern serving as a reference for comparison is specified in step S15. The reference pattern is specified by selecting a pattern estimated to be the most accurate pattern out of the displayed patterns. In this embodiment, the reference pattern is specified as described below.

Figure 8A:
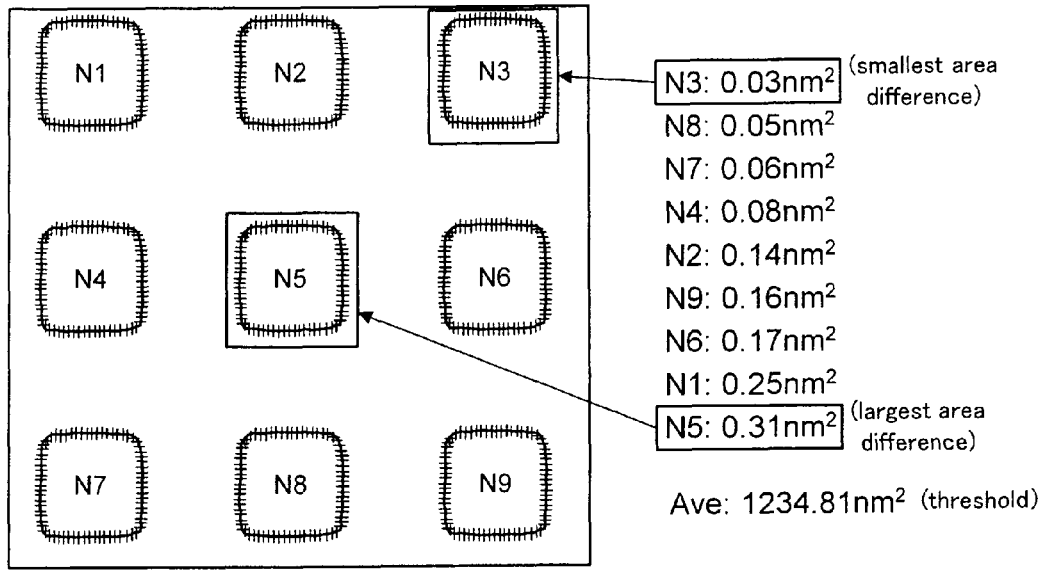
FIGS. 8A and 8B are views for explaining the process of extracting the pattern including the defect.

First, an average value of the calculated areas of the respective patterns is calculated and this average value is set as a threshold. Then, a difference between the threshold and the area value is calculated for each of the patterns. FIG. 8A shows an example in which the differences of the respective patterns between the threshold and the area value are sorted in ascending order. The threshold (the average value) is calculated as 1234.81 $nm^2$ on the basis of the areas of the patterns N1 to N9. Meanwhile, the area difference between the area of the pattern N3 and the average value is 0.03 $nm^2$ which is the smallest of all the patterns. In this way, the pattern least different from the average value in area i.e., the pattern which is closest to the average value is estimated as the accurate pattern and is therefore used as the reference pattern.

If a concrete value is known in advance, such a value may be used as the threshold. Alternatively, a plurality of thresholds may be set. For example, in addition to the above-described average value of areas, a threshold for excluding a pattern which is only partially displayed in the view field may be set.

Next, the defect candidate pattern is specified by comparing the reference pattern with other patterns in step S16.

There are three ways of specifying the defect candidate pattern, namely, (i) specifying a pattern most different from the reference pattern in area as the defect candidate pattern, (ii) specifying a pattern having the lowest degree of coincidence in shape with the reference pattern as the defect candidate pattern, and (iii) specifying the defect candidate pattern by using both aspects of the difference area and the degree of coincidence.

(i) Specifying a Pattern Most Different from the Reference Pattern in Area as the Defect Candidate Pattern This method corresponds to FIG. 8A in which the pattern N5 most different from the reference pattern N3 in area is specified as the defect candidate pattern.

Figure 8B:
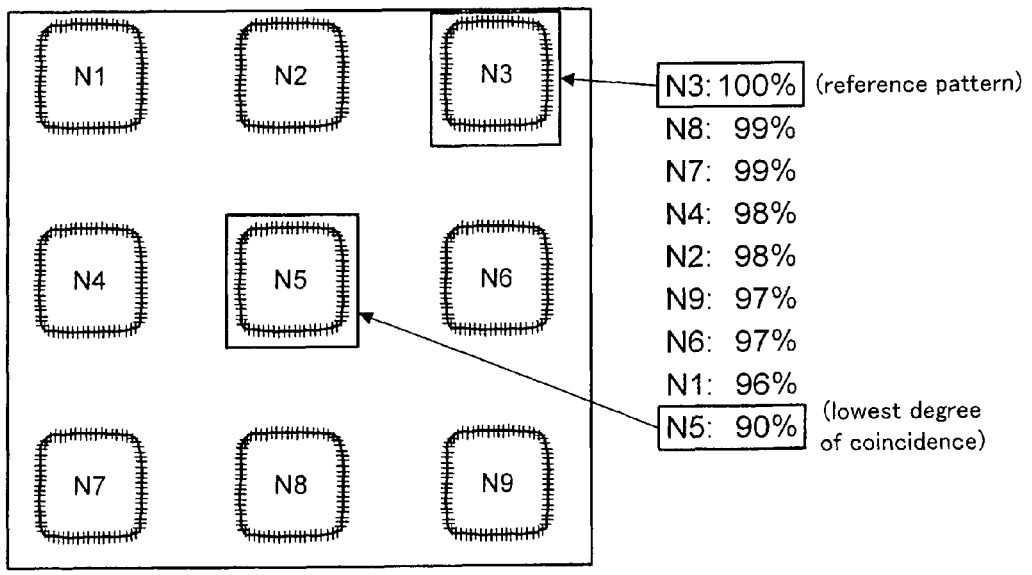

(ii) Specifying a Pattern Having the Lowest Degree of Coincidence in Shape with the Reference Pattern as the Defect Candidate Pattern This method corresponds to FIG. 8B. FIG. 8B shows an example in which the degree of coincidence in a pattern shape with the reference pattern is calculated by performing comparison with the reference pattern. As shown in FIG. 8B, the pattern N5 marks the lowest hit rate as a result of comparison with the reference pattern N3 and shows the lowest degree of coincidence. Such a pattern is specified as a pattern highly likely to have a defect. Here, a known method such as a convolution method using FFT is used to obtain the degree of coincidence in a pattern shape with the reference pattern (a correlation analysis).

(iii) Specifying the Defect Candidate Pattern by Using Both Aspects of the Difference in Area and the Degree of Coincidence In a case where the defect pattern is detected by using both aspects of the difference in area and the degree of coincidence, if the pattern most different in area from the reference pattern is the same as the pattern having the lowest degree of coincidence with the reference pattern, then that pattern is specified as the defect candidate pattern. On the other hand, if the pattern most different in area from the reference pattern is different from the pattern having the lowest degree of coincidence with the reference pattern, then the pattern located closer to the coordinate position acquired from the optical defect inspection device is specified as the defect candidate pattern.

The pattern having a high probability of including the defect is specified from the SEM image displayed in the view field range, by performing the above-described process of specifying the defect candidate pattern. This process is performed for each of the plurality of defect positions acquired from the optical defect inspection device, and the defect candidate pattern is specified in each of the SEM images.

Next, descriptions are given of the process of judging whether or not the defect candidate pattern specified in the above-described process is a defect to be transferred on the wafer.

Figure 9A:
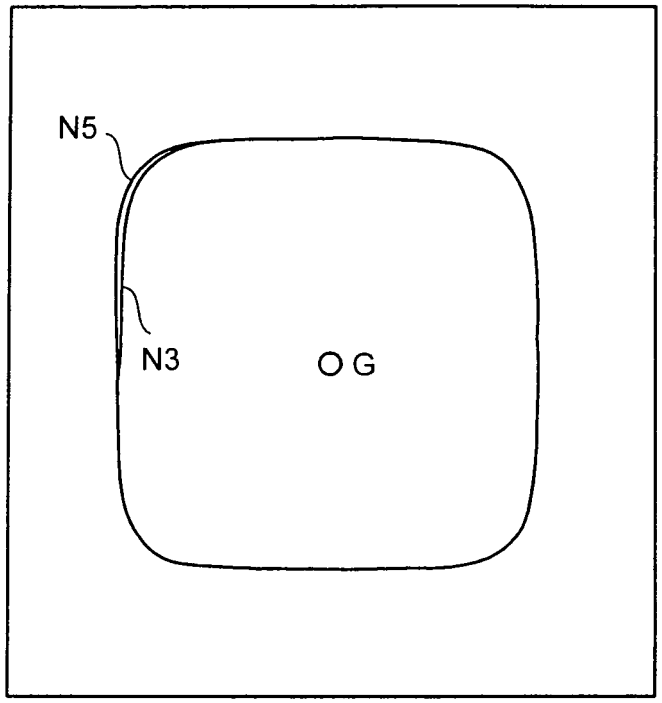
FIGS. 9A and 9B are views for explaining a process of judging whether or not the defect of the pattern is to be transferred onto a wafer.

FIG. 9A shows the defect candidate pattern N5 and the reference pattern N3 in an overlapping manner. Such an overlap may be achieved by aligning the centers of the respective patterns or by disposing the two patterns at such positions that the two patterns most broadly overlap each other on the basis of cross-correlation.

Figure 9B:
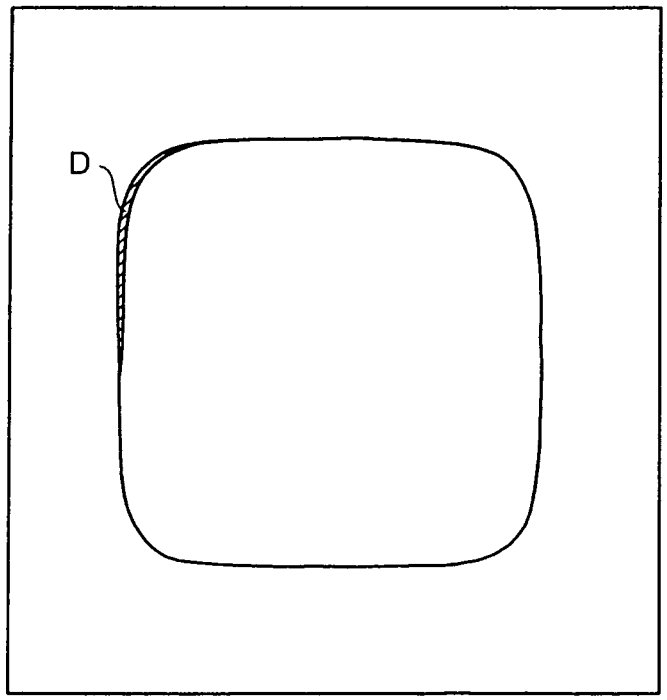

FIG. 9B shows a differential region D which appears as a result of overlapping the patterns. In respect of this differential region D, an area difference, a distance difference $\Delta X$ in an X direction, a distance difference $\Delta Y$ in a Y direction, and an inscribed circle of the differential region D are calculated.

A reference value (a transfer judgment value) is calculated in advance for each of the area difference, the distance difference and the inscribed circle. The reference value indicates such a value, with respect to a pattern having predetermined shape and size, that the defect is likely to be transferred on the wafer. Then the judgment is made as to whether or not the defect pattern is one to be transferred onto the wafer by comparing the actual value with the reference value.

Each of the transfer judgment values may be a value calculated by WPI simulation, a value obtained by a MEEF analysis or an empirically determined value. These transfer judgment values are inputted to the apparatus either automatically or manually.

Note that the WPI (Wafer Plane Inspection) is a mask inspection technique for a photomask inspection apparatus, and is a technique for evaluating a probability of transfer of the defect onto the wafer, in addition to a defect of the mask. The evaluation is made by forming an areal plane image on a photoresist surface on the basis of a mask pattern reproduced from images of transmitted light and reflected light of the mask, and then by calculating a wafer plane image from the areal plane image.

Meanwhile, the MEEF (Mask Error Enhancement Factor) is a factor at which an error on a mask is magnified on a wafer, and is a phenomenon in which an error having occurred in the manufacturing of mask is outputted in a more emphasized manner in a pattern to be formed on the wafer.

As described above, in the embodiment, in order to observe the pattern including the defect detected by the optical defect inspection device in the SEM image, the position of the defect of the pattern is acquired from the optical defect inspection device. This position does not completely match the coordinate position in the SEM. Therefore, the pattern including the defect is specified in the SEM in the manner described in the foregoing. Namely, areas of the respective similar patterns which are present in the view field of the SEM and an average area of the patterns which are supposed to have the identical shape are calculated. Then, the pattern whose area is closest to the average area is determined as the reference pattern. Next, correlations between the reference pattern and other patterns are obtained, and the pattern having the lowest correlation is set as the pattern including the defect. Then, the judgment is made as to whether or not the defect is the defect to be transferred onto the wafer.

As described above, the pattern including the defect is specified from the image information on the patterns displayed in the predetermined region, without preparing a pattern having no defects in advance.

In this way, it is possible to automatically detect the pattern including the defect which is not visually detectable.

What is claimed is:

1. A pattern inspection apparatus comprising:
   an irradiator configured to irradiate a sample with an electron beam;
   an electron detector configured to detect an amount of electrons generated on the sample by the irradiation of the electron beam, the sample having a pattern formed thereon;
   an image processor configured to generate a SEM image of the pattern on the basis of the amount of the electrons; and
   a controller configured to acquire defect position information on the pattern formed on the sample from an optical defect inspection device,
   wherein the controller specifies a defect candidate pattern from the SEM image on the basis of the defect position information and judges whether or not a defect in the defect candidate pattern is to be transferred onto a wafer; and
   wherein the controller determines a view field of the SEM image and sets an average value of areas of a plurality of similar patterns in the view field as a threshold and specifies a pattern having an area least different from the threshold as a reference pattern.

2. The pattern inspection apparatus according to claim 1, wherein the controller determines the view field of the SEM image on the basis of the defect position information and specifies the defect candidate pattern from image information on patterns displayed in the SEM image in the view field.

3. The pattern inspection apparatus according to claim 2, wherein the controller specifies the reference pattern serving as a reference from patterns displayed in the SEM image, compares the reference pattern with other similar patterns, and specifies, as the defect candidate pattern, at least any of a pattern largely different in area from the reference pattern and a pattern having a low degree of coincidence in pattern shape with the reference pattern.

4. The pattern inspection apparatus according to claim 1, wherein the controller performs a correlation analysis between the reference pattern and other patterns in the view field and specifies, as the defect candidate pattern, any one of a pattern having the lowest hit rate and a pattern most different from the reference pattern in area.

5. The pattern inspection apparatus according to claim 4, wherein, when there are a plurality of the defect candidate patterns, the controller compares a position of each of the defect candidate patterns with a defect position detected in the optical defect inspection device and specifies the defect candidate pattern located at a position closest to the defect position as the defect candidate pattern.

6. The pattern inspection apparatus according to claim 5, wherein the controller extracts a difference between the reference pattern and the defect candidate pattern, compares the difference with a transfer judgment reference defined in advance, and judges whether or not the defect in the defect candidate pattern is to be transferred onto the wafer.

7. The pattern inspection apparatus according to claim 6, wherein the transfer judgment reference is defined based on at least any of an area difference of the difference, a distance difference in an X direction or a Y direction, and an inscribed circle inside the difference.

8. A pattern inspection method applicable to a pattern inspection apparatus including an irradiator configured to irradiate a sample with an electron beam, an electron detector configured to detect an amount of electrons generated on the sample by irradiation of the electron beam, the sample having a pattern formed thereon, and an image processor configured to generate image data of the pattern on the basis of the amount of the electrons, the method comprising the steps of:
  acquiring defect position information on a pattern having a defect from an optical defect inspection device;
  determining a view field of a SEM image on the basis of the defect position information and acquiring the SEM image;
  specifying a reference pattern serving as a reference from patterns displayed in the SEM image;
  comparing the reference pattern with other patterns and thus specifying a defect candidate pattern including a defect; and
  judging whether or not the defect of the specified defect candidate pattern is a defect to be transferred onto a wafer;
  wherein, in the step of specifying the reference pattern, an average value of areas of a plurality of similar patterns in the view field is set as a threshold and a pattern least different from the threshold is set as the reference pattern.

9. The pattern inspection method according to claim 8, wherein, in the step of specifying the defect candidate pattern including a defect, a pattern most different from the reference pattern in area among other patterns in the view field is set as the defect candidate pattern.

10. The pattern inspection method according to claim 8, wherein, in the step of specifying the defect candidate pattern, a correlation analysis is performed between the reference pattern and other patterns in the view field and a pattern having the lowest degree of coincidence with the reference pattern is set as the defect candidate pattern.

11. The pattern inspection method according to claim 8, wherein the step of specifying the defect candidate pattern comprises the steps of:
  extracting a first defect candidate pattern having the defect by use of a difference between an area of the reference pattern and each of areas of the other patterns;
  extracting a second defect candidate pattern having the defect by a correlation analysis between the reference pattern and the other patterns in the view field, and
  setting, as the defect candidate pattern, a defect candidate pattern having a shorter distance to a defect position acquired from the optical defect inspection device, among the first defect candidate pattern and the second defect candidate pattern.

12. The pattern inspection method according to claim 8, wherein, in the step of judging whether or not the defect of the specified defect candidate pattern is a defect to be transferred onto a wafer, a difference between the reference pattern and the defect candidate pattern is extracted and a judgment is made by comparing the extracted difference with a transfer judgment reference defined in advance.

13. The pattern inspection method according to claim 12, wherein the transfer judgment reference is defined based on at least any of an area difference of the difference, a distance difference in an X direction or a Y direction, and an inscribed circle inside the difference.

* * * * *